United States Patent [19]
Domergue et al.

[11] 3,932,413
[45] Jan. 13, 1976

[54] PROCESS FOR THE PREPARATION OF 4'-ALKOXY-4-NAPHTHALIMIDO-PYRAZOLIUM COMPOUNDS AND INTERMEDIATES THEREFOR

[75] Inventors: Annick Marthe Suzanne Simone Domergue, Eaubonne; Robert Frederic Michel Sureau, Enghien-le-Bains; Jean Ernest Etienne Leboulenger, Taverny; Jean Marie Alfred Houssin, Enghien-le-Bains, all of France

[73] Assignee: Products Chimiques Ugine Kuhlmann, Paris, France

[22] Filed: May 21, 1973

[21] Appl. No.: 362,555

[30] Foreign Application Priority Data
May 24, 1972  France ........................ 72.18445

[52] U.S. Cl. .................... 260/270 H; 260/281
[51] Int. Cl.² ............. C07D 217/24; C07D 231/40
[58] Field of Search ......... 260/281, 281 N, 281 NH, 260/270 H

[56] References Cited
UNITED STATES PATENTS
3,649,633  3/1972  Mingasson et al. ............. 260/281
3,697,525  10/1972  Okada ........................ 260/281

FOREIGN PATENTS OR APPLICATIONS
45-2668  1/1970  Japan ........................ 260/281

*Primary Examiner*—Donald G. Daus
*Assistant Examiner*—Mark L. Berch
*Attorney, Agent, or Firm*—Browne, Beveridge, DeGrandi & Kline

[57] ABSTRACT

A process for the preparation of an optical brightening agent falling within the formula:

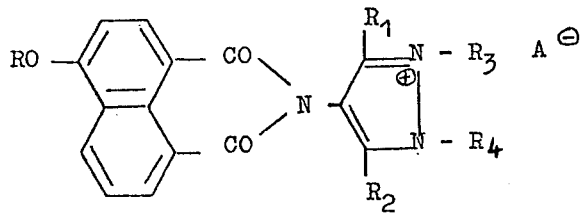

in which R represents an alkyl group containing 1 to 4 carbon atoms, $R_1$ and $R_2$ each represent a hydrogen atom, an alkyl group containing 1 to 4 carbon atoms or a phenyl group either unsubstituted or substituted by at least one alkyl group containing 1 to 4 carbon atoms, $R_3$ and $R_4$ each represent an alkyl group containing 1 to 4 carbon atoms and $A^-$ represents a monovalent anion which comprises reacting a compound of the formula:

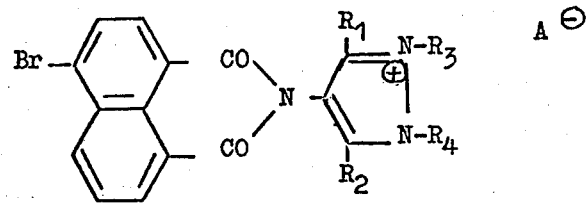

in which $R_1$, $R_2$, $R_3$, $R_4$, and $A^-$ have the meanings given above, with an alcoholate of the formula RO-Me in which R represents an alkyl group containing 1 to 4 carbon atoms and Me is an alkali metal; compounds falling within the formula:

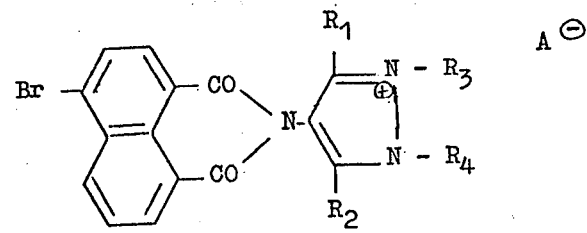

wherein $R_1$, $R_2$, $R_3$, $R_4$ and $A^-$ have the meanings given above.

5 Claims, No Drawings

PROCESS FOR THE PREPARATION OF 4'-ALKOXY-4-NAPHTHALIMIDO-PYRAZOLIUM COMPOUNDS AND INTERMEDIATES THEREFOR

The present invention relates to a new process for the preparation of 4'-alkoxy-4-napthalimido-pyrazolium compounds. These compounds are utilisable as optical brightening agents for fibres based on polymers or copolymers of acrylonitrile.

French Pat. No. 1,541,050 describes organic compounds of cationic nature corresponding to the general formula:

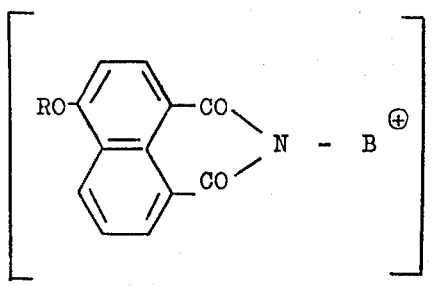

in which R represents an alkyl radical, $B^+$ represents a cyclic ammonium group and A represents a monovalent anion or its equivalent. According to the process of the prior art, these optical brightening agents are prepared from compounds of the general formula:

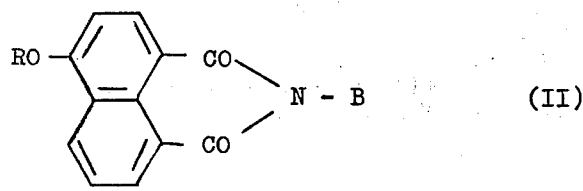

in which R has the same meaning as above and B represents a mono- or polycyclic heterocyclic nitrogen group, with which an alkylating agent of formula A-alkyl, for example an alkyl halide, sulphate or sulphonate, is reacted.

According to the present invention a process is provided for the preparation of an optical brightening agent falling within the formula:

a phenyl group either unsubstituted or substituted by at least one alkyl group containing 1 to 4 carbon atoms, $R_3$ and $R_4$ each represent an alkyl group containing 1 to 4 carbon atoms, and $A^-$ represents a monovalent anion which comprises reacting a compound of the formula:

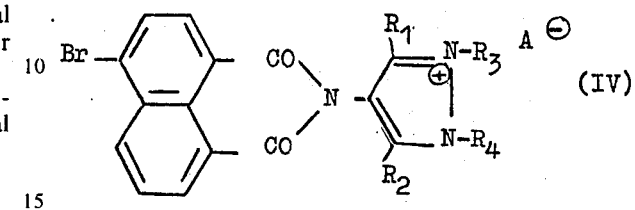

in which $R_1$, $R_2$, $R_3$, $R_4$ and $A^-$ have the meanings given above with an alkali metal alcoholate of the formula ROMe, in which R represents an alkyl group containing 1 to 4 carbon atoms and Me represents an alkali metal preferably sodium.

The reaction is preferably effected in an excess of alcohol ROH at a temperature between 20°C. and the boiling temperature of the alcohol.

The compounds of formula (IV), which are novel, may be obtained for example from bromonaphthalimides of the following formula:

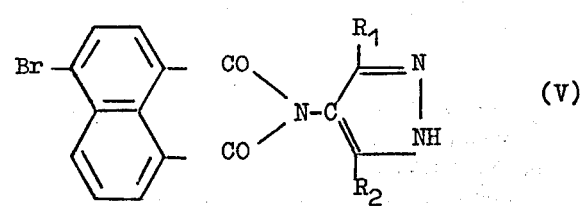

with which is reacted an alkylating agent of the formula A-alkyl, for example an alkyl halide, sulphate or sulphonate, if desired in the presence of a solvent such as an aromatic hydrocarbon or a chlorinated derivative thereof, an alcohol or dimethylformamide. An alkyl sulphate, for example dimethyl sulphate, is preferably used.

The bromonaphthalimides of formula (V) are easily converted to the quaternary compounds and give quaternary salts which are easy to separate in the pure state. The bromonaphthalimides of formula (IV) have the characteristic of reacting with alkali metal alcoholates to give the quaternary salts of the formula (III), in

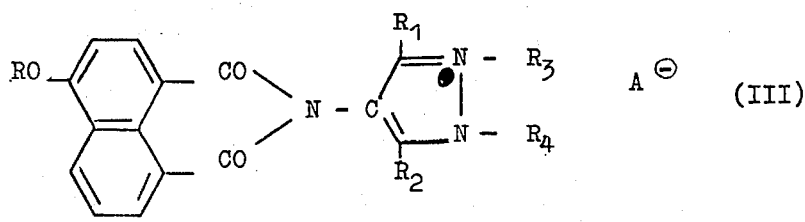

in which R represents an alkyl group containing 1 to 4 carbon atoms, $R_1$ and $R_2$ each represent a hydrogen atom, an alkyl group containing 1 to 4 carbon atoms or a pure form and with excellent yields. The possibility of this reaction is quite surprising since analogous quaternary salts containing a pyridinium, triazolium, thiazolium or 3- (or 5)-pyrazolio nucleus have a very poor stability under these same reaction conditions. It was therefore entirely unexpected to obtain the 4-pyrazolio compounds according to the process of the present invention.

The following Examples illustrate the present invention without restricting it thereto; the parts are parts by weight.

EXAMPLE 1

12.75 parts of 4'-bromo-4-naphthalimido-1,2,3,5tetramethyl-pyrazolium methylsulphate were introduced into 125 parts of methanol containing 1.15 parts of sodium. The mixture was heated under reflux for an hour, left to cool and the mineral salts were filtered off.

The light yellow solution was evaporated under vacuum, diluted by the addition of 100 parts of water and acidified with 2.5 parts of hydrochloric acid. Sodium chloride in the proportion of 20% was added, and then 6.3 parts of a solution of zinc chloride (d=1.26) were added gradually until precipitation was complete. The solid was filtered off and dried, and 10 parts of hydrated 4'-methoxy-4-naphthalimido-1,2,3,5-tetramethylpyrazolium chlorozincate (m.p. 265°C.) were obtained. After crystallising from methanol, analysis gave the following results:

For $C_{20}H_{20}Cl\ N_3O_3$, $½ZnCl_2,H_2O$. Calculated %: C: 50.9; H: 4.66; N: 8.90; Cl: 15.0. Found %: C; 50.4; H: 4.45; N: 8.66; Cl: 14.9.

EXAMPLE 2

18.5 parts of 4-bromo-N(3,5-dimethyl-4-pyrazolyl)-naphthalimide were introduced at 85°C. into 20 parts of dimethyl sulphate and the mixture was then heated for 3 hours at 130°C. After cooling, 50 parts of water were added and the product was left at the ambient temperature for 12 hours while stirring. The excess dimethyl sulphate was hydrolysed, and the solution was clarified with animal black, filtered and neutralised to pH 3 with sodium bicarbonate. A precipitate was thus obtained which was filtered off and dried, and was the pyrazolium methylsulphate of the above formula which melts at 254–255°C. 20 parts of 4'-bromo-4-naphthalimido-1,2,3,5-tetramethyl-pyrazolium methylsulphate were obtained. After crystallising from methanol, analysis gave the following results:

For $C_{20}H_{20}Br\ N_3O_6S$, $H_2O$. Calculated %: C: 45.6; H: 3.7; N: 7.9. Found %: C: 45.6; H: 3.8; N: 8.0.

EXAMPLE 3

The operation was as in Example 1, but the 125 parts of methanol were replaced by 125 parts of absolute ethanol. 7.5 parts of 4'-ethoxy-4-naphthalimido-1,2,3,5-tetramethylpyrazolium chlorozincate were obtained (m.p. 237°C.)

EXAMPLE 4

5 parts of 4'-bromo-4-napthalimido-5-phenyl-1,2,3-trimethyl-pyrazolium bromide were introduced into 50 parts of methanol containing 0.23 parts of sodium. The mixture was heated under reflux for an hour, then acidified with hydrochloric acid and the methanol was evaporated in vacuo. The residue was taken up in 20 parts of water. Sodium chloride in the proportion of 20% was added to the light yellow solution obtained. Then 1.22 parts of a zinc chloride solution (d=1.26) were added until precipitation was complete. 5 parts of 4'methoxy-4-naphthalimido-5-phenyl-1,2,3-trimethyl-pyrazolium chlorozincate were obtained (m.p. 220°C.).

EXAMPLE 5

17.3 parts of 4-bromo-N(5-phenyl-3-methyl-4-pyrazolyl)-naphthalimide and 16 parts of dimethyl sulphate were heated at 130°C. for 2 hours, then cooled, and 50 parts of water were added. It was left at the ambient temperature for 12 hours while stirring. The excess dimethyl sulphate was hydrolysed, and the solution obtained was clarified with animal black and then neutralised to pH 3 with 9.5 parts of sodium bicarbonate. 30 parts of sodium bromide were then added to the solution at 0°C. and the precipitate was filtered off. 22 parts of 4'-bromo-4-naphthalimido-5 -phenyl-1,2,3-trimethyl-pyrazolium bromide were obtained (m.p. 240°C.).

We claim:

1. A process for the preparation of an optical brightening agent falling within the formula:

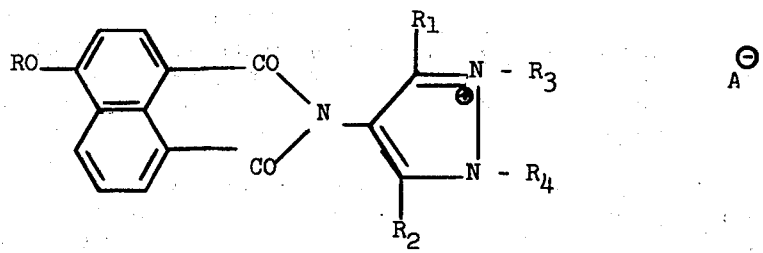

in which R represents an alkyl group of 1 to 4 carbon atoms, $R_1$ and $R_2$ each represent a hydrogen atom, an alkyl group of 1 to 4 carbon atoms or a phenyl group either unsubstituted or substituted by one or two alkyl groups of 1 to 4 carbon atoms, with the proviso that if either $R_1$ or $R_2$ are bis (t-butyl) phenyl, then the t-butyl groups are not in adjacent positions on the phenyl ring, $R_3$ and $R_4$ each represent an alkyl group of 1 to 4 carbon atoms and $A^-$ represents the monovalent anion chloride, bromide, chlorozincate or methylsulfate which consists of reacting a compound of the formula:

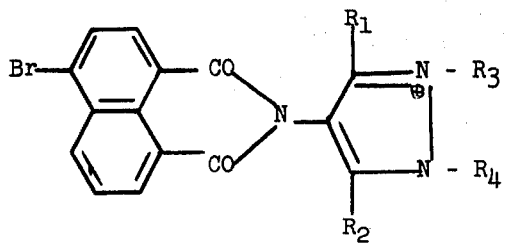

in which $R_1$, $R_2$, $R_4$, and $A^-$ have the meanings given above, with an alcoholate of the formula RO-Me in which R represents an alkyl group of 1 to 4 carbon atoms and Me is an alkali metal.

2. Process according to claim 1 wherein the reaction is effected in an excess of alcohol ROH.

3. Process according to claim 2 wherein the reaction is effected at a temperature between 20°C. and the boiling temperature of the alcohol.

4. Process according to claim 1 wherein Me is sodium.

5. Compounds falling within the formula:

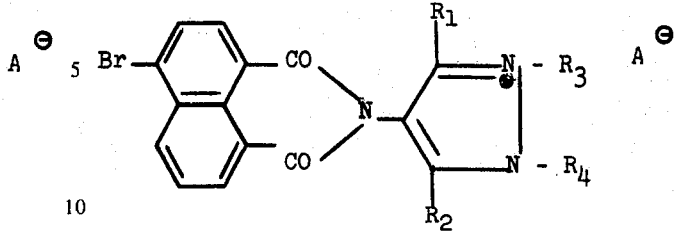

wherein $R_1$ and $R_2$ each represent a hydrogen atom, an alkyl group of 1 to 4 carbon atoms or a phenyl group either unsubstituted or substituted by one or two alkyl groups of 1 to 4 carbon atoms, with the proviso that if either $R_1$ or $R_2$ are bis (t-butyl) phenyl, then the t-butyl groups are not in adjacent positions on the phenyl ring, $R_3$ and $R_4$ each represent an alkyl group of 1 to 4 carbon atoms and $A^-$ represents the monovalent anion chloride, bromide, chlorozincate or methylsulfate.

* * * * *